United States Patent [19]

Pestellini et al.

[11] Patent Number: 4,485,112

[45] Date of Patent: Nov. 27, 1984

[54] N-[(BENZOFURAN-2-YL)(PHENYL)METHYL]-ALKYLENE DIAMINES USEFUL IN TREATING ARRHYTHMIC, HISTAMINIC AND TUSSIVE CONDITIONS

[75] Inventors: Vittorio Pestellini; Mario Ghelardoni; Carlo Alberto Maggi, all of Florence; Gabrio Roncucci, Siena; Alberto Meli, Florence, all of Italy

[73] Assignee: A. Menarini S.A.S., Italy

[21] Appl. No.: 468,869

[22] Filed: Feb. 22, 1983

Related U.S. Application Data

[63] Continuation-in-part of Ser. No. 253,551, Apr. 13, 1981, abandoned.

[30] Foreign Application Priority Data

Nov. 12, 1980 [IT] Italy .................................. 9583 A/80

[51] Int. Cl.³ ...................... A61K 31/34; C07D 307/81
[52] U.S. Cl. .................................... 424/285; 549/458; 549/467
[58] Field of Search ................. 549/458, 467; 424/285

[56] References Cited

FOREIGN PATENT DOCUMENTS 4139-63  2/1963  Italy .
1160925  8/1969  United Kingdom .

OTHER PUBLICATIONS

Silvestrini et al., Arch. Int. Pharmacodyn. Ther. 1960, vol. 129, pp. 249–263.

Ghelardoni et al., Boll., Chim. Farm., vol. 109, (1970), pp. 48–59.

*Primary Examiner*—Henry R. Jiles
*Assistant Examiner*—Bernard I. Dentz
*Attorney, Agent, or Firm*—McGlew and Tuttle

[57] ABSTRACT

A 2-substituted benzofuran derivative of general formula I or II

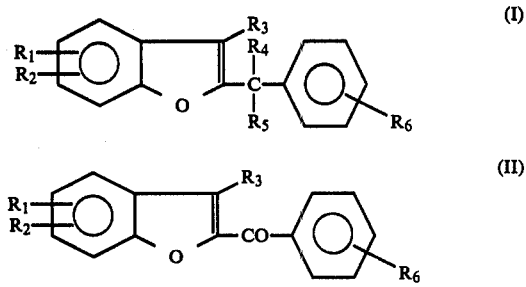

in which $R_1$ and $R_2$, can be the same or different, and are a hydrogen atom, a halogen atom, an alkyl group containing 1 to 4 carbon atoms, an arylalkyl group, an aryl group, a hydroxyl group, an alkoxy group, or an $NH_2$, NH-alkyl, N(alkyl)$_2$, NH(CO-alkyl), NH(CO-aryl) or $NO_2$ group, or $R_1$ and $R_2$ can together form a ring of 5–8 carbon atoms; $R_3$ is a hydrogen atom, an alkyl group containing 1 to 4 carbon atoms or an aryl group; $R_4$ is a hydrogen atom, an alkyl group, an aryl or an arylalkyl group, $R_5$ is a hydroxyl group, an alkoxy group, an OCO-aryl an OCO-alkyl, OCONH-alkyl or OCONH-aryl group,

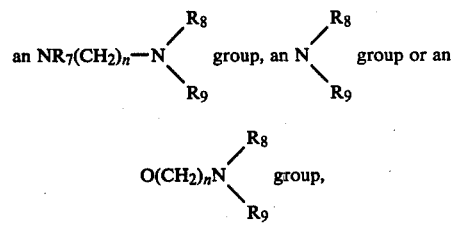

where n is a number between 1 and 4, $R_7$ is a hydrogen atom or an alkyl group containing 1 to 4 carbon atoms, and $R_8$ and $R_9$, which can be the same or different, represent a hydrogen atom, an alkyl group, an aryl group, an alkoyl group, arylalkoyl group or an aroyl group, or can together form a heterocyclic ring which can contain supplementary heteratoms, and $R_6$ is a hydrogen or halogen atom, an alkyl group, an arylalkyl group, an aryl group, a hydroxyl group, an alkoxy group, or an $NH_2$, NH-alkyl, N(alkyl)$_2$, NHCO-alkyl, NHCO-aryl or $NO_2$ group. The compounds are useful for treating arrhythmic, histaminic and tussive conditions.

16 Claims, No Drawings

N-[(BENZOFURAN-2-yl)(PHENYL)METHYL]-ALKYLENE DIAMINES USEFUL IN TREATING ARRHYTHMIC, HISTAMINIC AND TUSSIVE CONDITIONS

CROSS-REFERENCE TO RELATED APPLICATION

This is a continuation-in-part of copending parent application Ser. No. 253,551, filed Apr. 13, 1981 and now abandoned.

BACKGROUND OF THE INVENTION

Field of the Invention

This invention relates to new pharmacologically active 2-substituted benzofuran derivatives, and methods for their preparation.

Certain benzofuran derivatives have been described in Italian Pat. No. 4139/63 and in Boll.Chim.-Farm.109,48(1970).

BRIEF SUMMARY OF THE INVENTION

According to the present invention, there is provided a compound having the general formula I or II

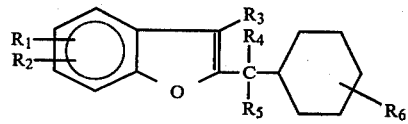

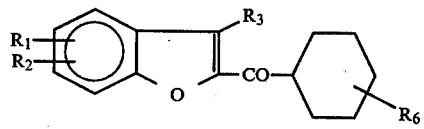

or a pharmaceutically acceptable salt thereof, in which:

$R_1$ and $R_2$ can be the same or different and are a hydrogen atom, a halogen atom, an alkyl group containing 1-4 carbon atoms, an arylalkyl group, an aryl group, a hydroxyl group, an alkoxy group, an $NH_2$, NH-alkyl, N(alkyl)$_2$, NH(CO-alkyl), NH(CO-aryl) or $NO_2$ group, or $R_1$ and $R_2$ can together form a ring of 5–8 carbon atoms;

$R_3$ is a hydrogen atom, an alkyl group containing 1 to 4 carbon atoms or an aryl group;

$R_4$ is a hydrogen atom, an alkyl group, an aryl group or an arylalkyl group;

R5 is a hydroxyl group, an alkoxy group, an OCO-alkyl, OCO-aryl, OCONH-alkyl or OCONH-aryl group,

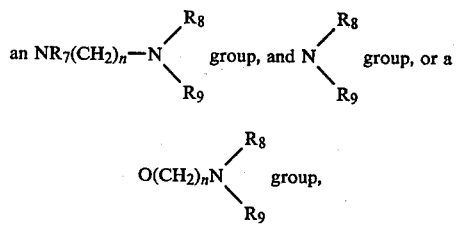

in which n is an integer of from 1 to 4, $R_7$ is a hydrogen atom or an alkyl group containing from 1 to 4 carbon atoms, and $R_8$ and $R_9$, which can be the same or different, represent a hydrogen atom, an alkyl group, an aryl group, an alkoyl group, an arylalkoyl group or an aroyl group, or together can form a heterocyclic ring which can contain supplementary heteroatoms;

$R_6$ is a hydrogen or halogen atom, an alkyl group, an arylalkyl group, an aryl group, a hydroxyl group, an alkoxy group, or a $NH_2$, NH-alkyl, N(alkyl)$_2$, NHCO-alkyl, NHCO-aryl or $NO_2$ group.

The pharmaceutically acceptable salts of the above-mentioned compounds are the non-toxic salts which can be formed when the compounds contain one or more basic groups.

Compounds having the general formulae I or II and containing one or more asymmetric carbon atoms, can be obtained in the form of optically active isomers.

DETAILED DESCRIPTION OF PREFERRED EMBODIMENTS

Specific examples of compounds of general formulae I and II embodying the invention include:

(1) N,N-diethyl-N' [(Benzofuran-2-yl)(p-chlorophenyl)methyl]ethylenediamine dihydrochloride Form. I: $R_1=R_2=R_3=R_4=H$; $R_5=NH(CH_2)_2—N(C_2H_5)_2 2HCl$; $R_6=4$-Cl

M.P. 184°–185° C.

H-NMR (D$_2$O), δ (p.p.m.): 1.25 (t, 2xCH$_3$) 3.15 (q, 2xCH$_3$) 3.6 (m, 2xCH$_2$) 5.8 (s, CH) 6.7–7.6 (m, 2xC$_6$H$_4$, CH)

(2) N[(benzofuran-2-yl)(p-chlorophenyl)methyl]morpholine hydrochloride

Form. I: $R_1=R_2=R_3=R_4=H$

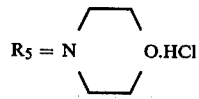

$R_6=4$-Cl
M.P.=194°–196° C.

(3) N-[(benzofuran-2-yl)(p-chlorophenyl)methyl]piperidine

Form. I; $R_1=R_2=R_3=R_4=H$

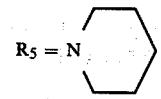

$R_6=4$-Cl
M.P. 116°–117° C.

(4) N[(benzofuran-2-yl) (p-tolyl)methyl]piperidine

Form. I: $R_1=R_2=R_3=R_4=H$

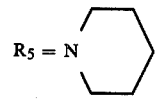

$R_6=4$-CH$_3$
M.P. 101°–102° C.

(5) N[(benzofuran-2-yl) (p-tolyl)methyl]morpholine hydrochloride

Form. I: $R_1=R_2=R_3=R_4=H$

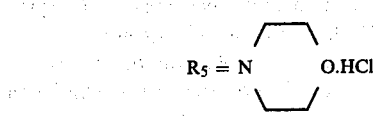

$R_6=4\text{-}CH_3$
M.P. 187°–189° C.

(6) 1-methyl-4[(benzofuran-2-yl) (p-tolyl)methyl]piperazine hydrochloride

Form. I: $R_1=R_2=R_3=R_4=H$

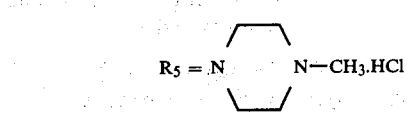

$R_6=4\text{-}CH_3$
M.P. 218°–220° C.

(7) 1-methyl-4[(benzofuran-2-yl) (p-chlorophenyl)methyl]piperazine dihydrochloride Form. I: $R_1=R_2=R_3=R_4=H$

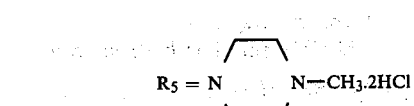

$R_6=4\text{-}Cl$
M.P. 176°–178° C.

(8) 1[(benzofuran-2-yl) (phenyl)methyl]piperidine

Form. I: $R_1=R_2=R_3=R_4=R_6=H$

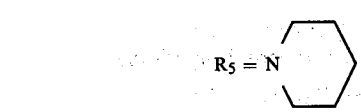

M.P. 77°–79° C.
H-NMR (CCl₄); δ (p.p.m.): 1.4 (m, 3xCH₂) 2.4 (m, 2xCH₂) 4.5 (s, CH) 6.5 (s, CH) 7–7.6 (m, C₆H₄, C₆H₅)

(9) 1(2-hydroxyethyl)-4[(benzofuran-2-yl) (phenyl)methyl]piperazine hydrochloride Form. I: $R_1=R_2=R_3=R_4=R_6=H$

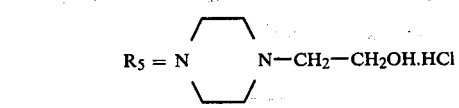

M.P. 179°–180° C.

(10) 1-methyl-4[(benzofuran-2-yl) (phenyl)methyl]piperazine

Form. I: $R_1=R_2=R_3=R_4=R_6=H$

M.P. 97°–99° C.
H-NMR (CDCl₃); δ (p.p.m.): 2.3 (s, CH₃) 2.4–2.6 (m, 4xCH₂) 4.55 (s, CH) 6.6 (s, CH) 7–7.6 (m, C₆H₄, C₆H₅)

(11) 1(2-hydroxypropyl)-4[(benzofuran-2-yl) (p-chlorophenyl)methyl]piperazine dihydrochloride Form. I: $R_1=R_2=R_3=R_4=H$

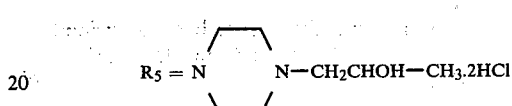

$R_6=4\text{-}Cl$
M.P. 170°–172° C.

(12) 1(2-hydroxyethyl)-4[(benzofuran-2-yl) (p-chlorophenyl)methyl]piperazine hydrochloride Form. I: $R_1=R_2=R_3=R_4=H$

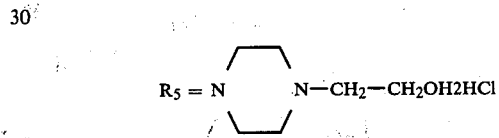

$R_6=4\text{-}Cl$
M.P. 164°–166° C.

(13) N[(benzofuran-2-yl) (phenyl)methyl]morpholine hydrochloride

Form. I: $R_1=R_2=R_3=R_4=R_6=H$

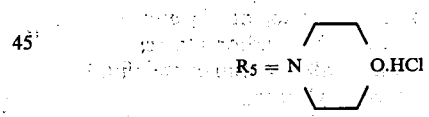

M.P. 183°–185° C.

(14) 1(2-hydroxypropyl)-4[(benzofuran-2-yl) (phenyl)methyl]piperazine dihydrochloride Form. I: $R_1=R_2=R_3=R_4=R_6=H$

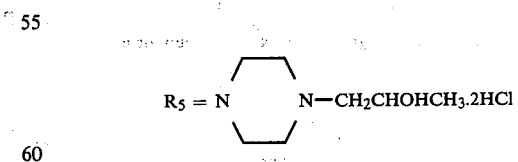

M.P. 184°–186° C.

(15) [(benzofuran-2-yl)(p-chlorophenyl)methyl]amine hydrochloride

Form. I: $R_1=R_2=R_3=R_4=H$; $R_5=NH_2HCl$; $R_6=4\text{-}Cl$
M.P. 225°–229° C.

(16)
1-phenyl-4[(benzofuran-2-yl)(p-chlorophenyl)methyl]-piperazine hydrochloride Form. I: $R_1=R_2=R_3=R_4=H$

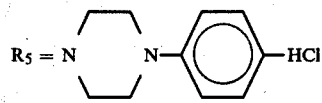

$R_6$=4-Cl
M.P. 170°–172° C.

(17)
N,N-diethyl-N'[(benzofuran-2-yl)(phenyl)methyl]ethylenediamine hydrochloride Form. I: $R_1=R_2=R_3=R_4=R_6=H$; $R_5=NH(CH_2)_2N(C_2H_5)_2.HCl$
M.P. 190°–192° C.

(18)
N,N-dimethyl-N'[(benzofuran-2-yl)(p-chlorophenyl)-methyl]ethylenediamine hydrochloride Form. I: $R_1=R_2=R_3=R_4=H$; $R_5=NH(CH_2)_2N(CH_3)_2$ HCl; $R_6$=4-Cl
M.P. 180°–182° C.

(19)
N,N-dimethyl-N'[(benzofuran-2-yl)(p-chlorophenyl)-methyl]propylenediamine hydrochloride Form. I: $R_1=R_2=R_3=R_4=H$; $R_5=NH(CH_2)_3N(CH_3)_2.HCl$; $R_6$=4-Cl
M.P. 139°–141° C.

(20)
N,N-dimethyl-N'[(benzofuran-2-yl)(phenyl)methyl]ethylenediamine hydrochloride Form. I: $R_1=R_2=R_3=R_4=R_6=H$; $R_5=NH(CH_2)_2N(CH_3)_2.HCl$
M.P. 189°–191° C.

(21)
N[(benzofuran-2-yl)(p-chlorophenyl)methyl]-2(diethylmethylammonium) ethylamine bromide Form. I: $R_1=R_2=R_3=R_4=H$; $R_5=NH(CH_2)_2N(CH_3)(C_2H_5)_2$ Br; $R_6$=4-Cl
M.P. 140°–142° C.

(22)
N[(5-bromobenzofuran-2-yl)(phenyl)methyl]-N',N'-diethylethylenediamine hydrochloride Form. I: $R_1$=5-Br $R_2=R_3=R_4=R_6=H$; $R_5=NH(CH_2)_2N(C_2H_5)_2.HCl$
M.P. 175°–177° C.

(23)
N[(benzofuran-2-yl)(p-tolyl)methyl]-N',N'-diethylethylenediamine hydrochloride Form. I: $R_1=R_2=R_3=R_4=H$; $R_5=NH(CH_2)_2N(C_2H_5)_2.HCl$; $R_6$=4-$CH_3$
M.P. 200°–202° C.
H-NMR ($D_2O$); δ (p.p.m.): 1.15 (t, 2x$CH_3$) 2.0 (s, $CH_3$) 3.1 (q, 2x$CH_2$) 3.4 (m, 2x$CH_2$) 5.6 (s, CH) 6.7 (s, CH) 6.8–7.4 (m, 2x$C_6H_4$)

(24)
1(2-pyridyl)-4-[(benzofuran-2-yl)(phenyl)methyl]piperazine

Form. I: $R_1=R_2=R_3=R_4=R_6=H$

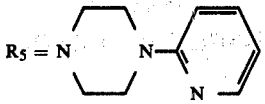

M.P. 174°–175° C.

(25) N-methanecarbamate of (benzofuran-2-yl)(p-chlorophenyl)methyl

Form. I: $R_1=R_2=R_3=R_4=H$; $R_5=OCONHCH_3$; $R_6$=4-Cl
M.P. 98°–99° C.

(26)
(Naphthofuran[2,1-b]-2-yl)(p-chlorophenyl)methanol

Form. I: $R_1$ and $R_2=C_4H_4$; $R_3=R_4=H$ $R_5=OH$; $R_6$=4-Cl
M.P. 101°–103° C.

(27) (benzofuran-2-yl)(p-tolyl)methanol

Form. I: $R_1=R_2=R_3=R_4=H$; $R_5=OH$; $R_6$=4-$CH_3$
M.P. 50°–52° C.

(28) (benzofuran-2-yl)(p-fluorophenyl)methanol

Form. I: $R_1=R_2=R_3=R_4=H$; $R_5=OH$; $R_6$=4-F
M.P. 47°–49° C.
H-NMR ($CCl_4$); δ (p.p.m.): 3.75 (s, OH) 5.65 (s, CH) 6.3 (s, CH) 6.7–7.5 (m, 2x$C_6H_4$)

(29) 1(benzofuran-2-yl)-1(p-chlorophenyl)ethanol

Form. I: $R_1=R_2=R_3=H$; $R_4=CH_3$; $R_5=OH$; $R_6$=4-Cl
M.P. 63°–66° C.
H-NMR ($CDCl_3$); δ (p.p.m.): 1.9 (s, $CH_3$) 2.85 (s, OH) 6.55 (s, CH) 7.0–7.6 (m, 2x$C_6H_4$)

(30)
(5-bromobenzofuran-2-yl)(p-chlorophenyl)methanol

Form. I: $R_1=R_3=R_4=H$; $R_2$=5-Br; $R_5=OH$; $R_6$=4-Cl
M.P. 82°–83° C.

(31) (benzofuran-2-yl)(o-tolyl)methanol

Form. I: $R_1=R_2=R_3=R_4=H$; $R_5=OH$; $R_6$=2-$CH_3$
M.P. 72°–75° C.

(32)
(3-methylbenzofuran-2-yl)(p-chlorophenyl)methanol

Form. I: $R_1=R_2=R_4=H$; $R_3=CH_3$; $R_5=OH$; $R_6$=4-Cl
M.P. 89°–91° C.
H-NMR ($CDCl_3$); δ (p.p.m.): 2.2 (s, $CH_3$) 3.1 (d, OH) 6.0 (d, CH) 7.2–7.6 (m, 2x$C_6H_4$)

(33) 1-(p-chlorophenyl)-1(benzofuran-2-yl)-2-phenyl ethanol

Form. I: $R_1=R_2=R_3=H$; $R_4=CH_2$-$C_6H_5$; $R_5=OH$; $R_6$=4-Cl
M.P. 129°–131° C.

(34) (benzofuran-2-yl)(biphenyl-4-yl)methanol

Form. I: $R_1=R_2=R_3=R_4=H$; $R_5OH$; $R_6=4$-$C_6H_5$
M.P. 123°–125° C.

(35) (4,6dimethoxybenzofuran-2-yl)(p-chlorophenyl)methanol

Form. I: $R_1=4$-$OCH_3$; $R_2=6$-$OCH_3$; $R_3=R_4=H$; $R_5=OH$; $R_6=4$-Cl
M.P. 82°–83° C.
H-NMR (CDCL$_3$); δ (p.p.m.): 2.9 (d, OH) 3.8 (s, CH$_3$) 3.85 (s, CH$_3$) 5.85 (d, CH) 6.3–7.4 (m, C$_6$H$_4$, C$_6$H$_2$, CH)

(36) (5-bromobenzofuran-2-yl)(phenyl)methanol

Form. I: $R_1=5$-Br; $R_2=R_3=R_4=R_6=H$; $R_5=OH$
M.P. 56°–58° C.

(37) (7-ethoxybenzofuran-2-yl)(p-chlorophenyl)methanol

Form. I: $R_1=7$-$OC_2H_5$; $R_2=R_3=R_4=H$; $R_5=OH$; $R_6=4$-Cl
H-NMR (CDCl$_3$): δ (p.p.m.) 1.4 (t, CH$_3$) 3.5 (s, OH) 4.1 (q, CH$_2$) 5.85 (s, CH) 6.4 (s, CH) 6.6–7.4 (m, C$_6$H$_4$, C$_6$H$_3$)

(38) (benzofuran-2-yl)(p-nitrophenyl)methanol

Form. I. $R_1=R_2=R_3=R_4H$; $R_5=OH$; $R_6=4NO_2$
M.P. 108°–110° C.

(39) (7-ethoxybenzofuran-2-yl)(p-nitrophenyl)methanol

Form: I. $R_1=7$-$OC_2H_5$; $R_2=R_3=R_4=H$; $R_5=OH$; $R_6=4NO_2$
M.P. 127°–128° C.

(40) N,N-dimethyl-N'[(benzofuran-2-yl)(p-fluorophenyl)methyl]ethylenediamine dihydrochloride Form. I. $R_1=R_2=R_3=R_4=H$; $R_5=NH(CH_2)_2 N(CH_3)_2.2HCl$; $R_6=4$-F
M.P. 179°–181° C.
H-NMR (D$_2$O); δ (p.p.m.): 3.2 (s, 2xCH$_3$) 3.7–3.9 (m, 2xCH$_2$) 6.05 (s, CH) 7.0 (s, CH) 7.1–8.0 (m, 2xC$_6$H$_4$)

(41) [(benzofuran-2-yl)(p-chlorophenyl)methyl]isopropylamine hydrochloride

Form. I: $R_1=R_2=R_3=R_4=H$; $R_5=NHCH(CH_3)_2.HCl$; $R_6=4$-Cl
M.P. 219°–220° C.

(42) 1(7-methoxybenzofuran-2-yl)-1(p-chlorophenyl)-2-phenyl ethanol

Form. I.: $R_1=7$-$OCH_3$; $R_2=R_3=H$; $R_4=CH_2C_6H_5$; $R_5=OH$; $R_6=4$-Cl
M.P. 130°–132° C.
I.R. (nujol) ν (cm$^{-1}$): 3540 (OH)
H-NMR (CDCl$_3$); δ (p.p.m.): 2.8 (s, OH) 2.6 (q, CH$_2$) 4.0 (s, CH$_3$) 6.5 (s, CH) 6.6–7.8 (m, C$_6$H$_5$, C$_6$H$_3$)

(43) 1(7-methoxybenzofuran-2-yl)-1(p-chlorophenyl)ethanol

Form. I.: $R_1=7$-$OCH_3$; $R_2=R_3=H$; $R_4=CH_3$; $R_5=OH$; $R_6=4$-Cl
M.P. 76°–78° C.

(44) (Naphthofuran[2,1-b]-2-yl)(phenyl)methanol

Form. I.: $R_1$ and $R_2=C_4H_4$; $R_3=R_4=R_6=H$; $R_5=OH$
M.P. 97°–99° C.

(45) (7-methoxybenzofuran-2-yl)(p-chlorophenyl)methanol

Form. I: $R_1=7$-$OCH_3$; $R_2=R_3=R_4=H$; $R_5=OH$; $R_6=4$-Cl
H-NMR (CDCl$_3$); δ (p.p.m.): 3.05 (m, OH) 3.9 (s, CH$_3$) 5.85 (s, CH) 6.4 (s, CH) 6.6–7.4 (m, C$_6$H$_4$, C$_6$H$_3$)

(46) (7-ethoxybenzofuran-2-yl)(biphenyl-4-yl)ketone

Form. II.: $R_1=7$-$OC_2H_5$; $R_2=R_3=H$; $R_6=4$-$C_6H_5$
M.P. 85°–86° C.
I.R. (nujol) ν (cm$^{-1}$): 1640 (C=O)
H-NMR (CDCl$_3$); δ (p.p.m.): 1.5 (t, CH$_3$) 4.30 (q, CH$_2$) 6.8–8.2 (m, C$_6$H$_5$, C$_6$H$_4$, C$_6$H$_3$, CH)

(47) (7-ethoxybenzofuran-2-yl)(p-chlorophenyl)ketone

Form. II: $R_1=7$-$OC_2H_5$; $R_2=R_3=H$; $R_6=4$-Cl
M.P. 108°–110° C.
I.R. (nujol) ν; (cm$^{-1}$): 1660 (C=O)
H-NMR (CDCl$_3$); δ (p.p.m.): 1.5 (t, CH$_3$) 4.25 (q, CH$_2$) 6.8–8.2 (m, C$_6$H$_4$, C$_6$H$_3$, CH)

(48) (7-methoxybenzofuran-2-yl)(p-chlorphenyl)ketone

Form. II: $R_1=7$-$OCH_3$ $R_2=R_3=H$ $R_6=4$-Cl
M.P. 77°–78° C.
I.R. (nujol) ν (cm$^{-1}$): 1635 (C=O)
H-NMR (CDCl$_3$); δ (p.p.m.): 4.0 (s, CH$_3$) 6.9–8.2 (m, C$_6$H$_4$, C$_6$H$_3$)

(49) (7-ethoxybenzofuran-2-yl)(p-nitrophenyl)ketone

Form. II: $R_1=7$-$OC_2H_5$; $R_2=R_3=H$; $R_6=4$-$NO_2$
M.P. 164°–166° C.
I.R. (nujol) ν (cm$^{-1}$): 1660 (C=O)
H-NMR (D M SO); δ (p.p.m.): 1.7 (t, CH$_3$) 4.5 (q, CH$_2$) 7.4–8.8 (m, C$_6$H$_4$, C$_6$H$_3$)

(50) (benzofuran-2-yl)(biphenyl-4-yl)ketone

Form. II: $R_1=R_2=R_3=H$; $R_6=4$-$C_6H_5$
M.P. 153°–155° C.
I.R. (nujol) ν (cm$^{-1}$): 1640 (C=O)

(51) (benzofuran-2-yl)(2-methoxyphenyl)ketone

Form. II: $R_1=R_2=R_3=H$ $R_6=2$-$OCH_3$
M.P. 78°–80° C.
I.R. (nujol) ν (cm$^{-1}$): 1645 (C=O)
H-NMR (CDCl$_3$); δ (p.p.m.): 3.75 (s, CH$_3$) 6.8–7.7 (m, 2xC$_6$H$_4$)

(52) (4,6-dimethoxybenzofuran-2-yl)(p-chlorophenyl)ketone

Form. II: $R_1=4$-$OCH_3$ $R_2=6$-$OCH_3$ $R_3=H$ $R_6=4$-Cl
M.P. 161°–163° C.

(53) N,N-dimethyl-N'[(5-bromobenzofuran-2-yl)(phenyl)methyl]ethylenediamine dihydrochloride Form. I: $R_1=5$-Br $R_2=R_3=R_4=R_6=H$ $R_5=NH(CH_2)_2 N(CH_3)_2.2HCl$
M.P. 181°–183° C.
H-NMR (D$_2$O); δ (p.p.m.): 3.3 (s, 2xCH$_3$) 3.9–4.0 (m, 2xCH$_2$) 6.0 (s, CH) 7.0 (s, CH) 7.05–8.0 (m, C$_6$H$_5$, C$_6$H$_3$)

(54)
(5-methoxybenzofuran-2-yl)(p-chlorophenyl)ketone

Form. II: $R_1=5\text{-OCH}_3$ $R_2=R_3=H$ $R_6=4\text{-Cl}$
M.P. 140°–142° C.
I.R. (nujol) $\nu$ (cm$^{-1}$): 1640 (C=O)
H-NMR (CDCl$_3$): $\delta$ (p.p.m.): 3.9 (s, CH$_3$) 7.0–8.2 (m, C$_6$H$_4$, C$_6$H$_3$, CH)

(55)
(6-methoxybenzofuran-2-yl)(p-chlorophenyl)ketone

Form. II: $R_1=6\text{-OCH}_3$; $R_2=R_3=H$; $R_6=4\text{-Cl}$
M.P. 186°–187° C.
I.R. (nujol) $\nu$ (cm$^{-1}$): 1630 (C=O)

(56) 1(7-ethoxybenzofuran-2-yl)-1(p-chlorophenyl)-2 phenyl-ethanol

Form. I: $R_1=7\text{-OC}_2\text{H}_5$; $R_2=R_3=H$; $R_4=\text{CH}_2\text{-C}_6\text{H}_5$; $R_5=\text{OH}$; $R_6=4\text{-Cl}$
M.P. 112°–114° C.
I.R. (nujol) $\nu$ (cm$^{-1}$): 1620 (C=O)

(57)
N,N,N'-trimethyl-N'-[(benzofuran-2-yl)(p-chlorophenyl)methyl]ethylenediamine dihydrochloride hydrate Form. I: $R_1=R_2=R_3=R_4=H$; $R_5=\text{N(CH}_3)\text{-(CH}_2)_2\text{-N(CH}_3)_2.2\text{HCl}.0.5\text{ H}_2\text{O}$
M.P. 165°–167° C.
H-NMR (D$_2$O); $\delta$ (p.p.m.): 3.2 (s, CH$_3$) 3.35 (s, 2xCH$_3$) 6.2 (s, CH) 7.2–8.1 (m, 2xC$_6$H$_4$, CH)

(58)
N[3(morpholin-4-yl)propyl]α(benzofuran-2-yl)p-chlorobenzylaminedihydrochloride hydrate Form. I: $R_1=R_2=R_3=R_4=H$;

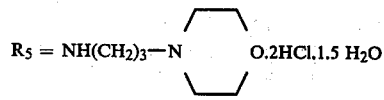

$R_6=4\text{-Cl}$
M.P. 135°–136° C.

(59) (Naphtho[2,1-b]furan-2-yl)-(phenyl)ketone

Form. II: R$_1$ and $R_2=C_4H_4$; $R_3=R_6=H$
M.P. 101°–102° C.
I.R. (nujol) $\nu$ (cm$^{-1}$): 1630 (C=O)

(60)
(Naphtho[2,1-b]furan-2-yl)-(p-chlorophenyl)ketone

Form. II: R$_1$ and $R_2=C_4H_4$ $R_3=H$ $R_6=4\text{-Cl}$
M.P. 156°–158° C.
I.R. (nujol) $\nu$ (cm$^{-1}$): 1630 (C=O) $R_6=4\text{-Cl}$ Methods of preparing compounds of general formulae I and II will now be described:

(a) If $R_4=H$ and $R_5=\text{OH}$ in formula I, then the compounds can be obtained by reducing the corresponding ketone compounds of general formula II. This reduction can be carried out for example by catalytic reduction of the corresponding ketone in a suitable solvent, (e.g. ethanol, methanol, dioxane) in the presence of catalysts (e.g. palladium-carbon, platinum black or Raney nickel) or by reduction with a reducing agent such as a complex metal hydride in a solvent, e.g. with sodium borohydride or sodium diethoxyaluminium hydride in alcohol, or with lithium-aluminium hydride in ether or dioxane, or by electrolytic reduction. The reduction can also be carried out using mineral acids (e.g. hydrochloric acid or sulphuric acid) and a metal (e.g. iron or tin) in water or dilute alcohol, or using metal sodium in alcohol or aluminium isopropylate in isopropanol.

(b) If $R_4$ is an alkyl, aryl or arylalkyl group and $R_5=\text{OH}$ in general formula I, the compounds can be obtained by adding organometallic compounds to the carbonyl group of compounds of general formula II, as indicated heretofore.

(c) If $R_5$ represents a

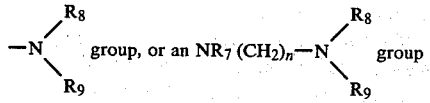

where n is a number between 1 and 4, $R_7$ is a hydrogen atom or an alkyl group containing 1 to 4 C atoms, and $R_8$ and $R_9$, which can be the same or different, represent a hydrogen atom, an alkyl group, an aryl group, an alkoyl group, an arylalkoyl group or an aroyl group, or can together form a heterocyclic ring which can contain supplementary heteroatoms, the compounds can be obtained by reacting a compound of general formula III

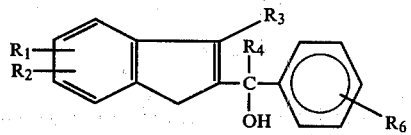

in which $R_1$, $R_2$, $R_3$, $R_4$ and $R_6$ are as heretofore defined, with a halogenating agent such as thionyl chloride, phosphorus pentachloride, phosphorus trichloride, iodine and phosphorus, bromine and phosphorus, hydrochloric acid or hydrobromic acid, to give the corresponding halogen derivative, and then reacting this latter with the appropriate base.

(d) If $R_5$ represents an OCO-alkyl, OCO-aryl, OCONH-alkyl or OCONH-aryl group in general formula I, the compounds can be obtained by reacting the alcohols of general formula III with the appropriate acid chloride, anhydride or isocyanate.

The compounds of general formula II can be prepared for example:

(e) by condensing an aldehyde or ketone of general formula

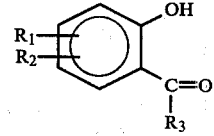

in a basic environment with an alpha-halogen acetophenone of formula

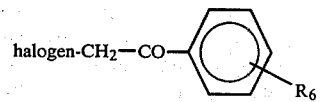

where $R_1$, $R_2$, $R_3$ and $R_6$ are as heretofore defined.

(f) By treating, with bromine, compounds of general formula

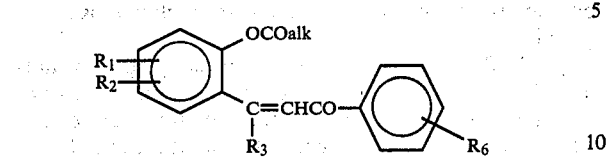

in which $R_1$, $R_2$, $R_3$ and $R_6$ are as heretofore defined, then treating the obtained corresponding dibromo derivative in an acid environment.

(g) By acylation, in the presence of aluminium chloride or another Lewis acid catalyst, of an appropriate benzofuran derivative of general formula

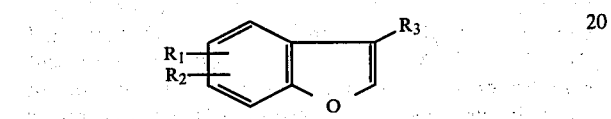

in which $R_1$, $R_2$ and $R_3$ are as heretofore defined, with an acylating agent of general formula

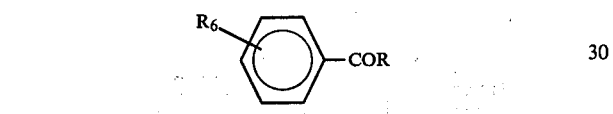

in which $R_6$ is as heretofore defined, and R is halogen, OCO-alkyl or OCO-aryl.

According to the methods of synthesis employed, the compounds will be obtained in the form of a free base or salt, depending on the starting materials and the reaction conditions.

Compounds obtained in the form of a free base can be converted into their pharmaceutically acceptable salts of various organic and inorganic acids. Suitable acids comprise inorganic acids (for example hydrochloric acid, hydrobromic acid, hydroiodic acid, sulphuric acid and phosphoric acid), and organic acids (for example citric acids, maleic acid, fumaric acid, tartaric acid, acetic acid, benzoic acid, lactic acid, methanesulphonic acid, salicylic acid or acetylsalicylic acid). The quaternary salts are also obtainable from the tertiary bases and alkyl halides or sulphates.

Methods of making compounds of general formulae I or II will now be particularly described by way of example.

Example 1:

1-methyl-4[(benzofuran-2-yl)(phenyl)methyl]piperazine 25.4 g of α(benzofuran-2-yl)benzyl chloride dissolved in 150 ml of dioxane are added slowly at about 60°–70° C. to 26 g of 1-methyl-piperazine in 150 ml of dioxane. After the addition, the mixture is stirred at about 70° C. for a further two hours. The solvent is removed under reduced pressure, the residue is then dissolved in 5% sodium bicarbonate and extracted with ethyl ether. After washing the ether phase with water and drying with sodium sulphate, the hydrochloride is precipitated by bubbling in anhydrous hydrochloric acid gas: M.P. 186°–188° C. (isopropanol).

Example 2:

N,N-diethyl-N'[(benzofuran-2-yl)(p-chlorophenyl)methyl]ethylenediamine dihydrochloride 5.21 g of α(benzofuran-2-yl)-p-chlorobenzylchloride dissolved in 100 ml of dioxane are added at ambient temperature to 9.28 g of N,N'-diethylenediamine in 70 ml of dioxane. After the addition, the mixture is kept for a further 2 hours at 60° C. The solvent is removed under reduced pressure, the residue is redissolved in 5% NaHCO$_3$ and then extracted with ethyl ether. After washing with water, the ether phase is dried with sodium sulphate, and the hydrochloride is precipitated by bubbling in anhydrous hydrochloric acid gas: M.P. 184°–185° C. (isopropanol).

Example 3:

1(benzofuran-2-yl)-1-(p-chlorophenyl)ethanol 14.2 g of methyl iodide in 50 ml of tetrahydrofuran are dripped slowly onto 2.43 g of magnesium chips in about 30 ml of tetrahydrofuran. When all the magnesium has dissolved, 25.6 g of 2(p-chloro-benzoyl)benzofuran, dissolved in 350 ml of tetrahydrofuran are added slowly. After the addition, the mixture is kept under reflux for 2 hours. It is cooled, poured into 500 g of crushed ice and 10 ml of concentrated HCl, then extracted with ethyl ether. The organic phase is washed with water, dried with anhydrous sodium sulphate, and evaporated to dryness, to leave a residue which crystallises from petroleum ether: M.P. 64°–66° C.

Example 4:

(7-ethoxybenzofuran-2-yl)(p-chlorophenyl)ketone 23.3 g of ω-bromo-p-chloroacetophenone are added to 17 g of 3-ethoxysalicylaldehyde in 800 ml of ethanol and 4 g of sodium hydrate. After heating the mixture for one hour under reflux, it is allowed to cool, the product which separates is filtered off, and is crystallised from ethanol: M.P. 108°–110° C.

Example 5:

(5-bromobenzofuran-2-yl)(phenyl)methanol 4 g of sodium borohydride dissolved in the minimum quantity of water are slowly added at ambient temperature to 8.5 g of 2-benzoyl-5-bromobenzofuran in 50 ml of dioxane. When the addition is finished, the mixture is kept stirring at ambient temperature for a further 3 hours. The solvent is removed under reduced pressure, the residue is redissolved in 50 ml of water, and extracted with ethyl ether. The ether phase is dried with anhydrous sodium sulphate, evaporated to dryness, and leaves a residue which on crystallising from cyclohexane has a M.P. of 56°–58° C.

The above described compounds show interesting pharmacological properties. In particular, compounds of general formula I and II show antihistaminic, local anaesthetic, antiarrhythmic, muscle relaxant and antidyslipidemic activity, and antagonist activity towards contractions by CaCl$_2$.

Pharmaceutical compositions can be produced comprising as their active ingredients at least one compound of general formula I and II (as heretofore defined), in association with a carrier or excipient.

These pharmaceutical compositions can be presented in suitable forms for oral, rectal or parenteral administration. They can be presented for example in the form of tablets, pills, sugar-coated pills, capsules, suspensions, oral or injectable solutions or powders. The carriers or excipients used can be those conventionally accepted for pharmacological use. The compositions are preferably presented in unit doses. The clinical dose of the compounds depends on the body weight, age and method of administration, but generally lies between 10 and 3000 mg/day.

The compounds according to the present invention for example possess, in fact, antiarrhythmic properties which can be ascribed to two different action mechanisms, that is, a local anaesthetic action (antiarrhythmic activity of class I according to Vaughan Williams, Int. Enc. Pharmacol. Ther. Section 105, pp125, 150; 1981) and a calcium antagonist action (antiarrhythmic activity of class IV according to Vaughan Williams, l.c.). The instant compounds also possess a moderate blocking $H_1$ antihistaminic activity and, to a larger extent, an interesting antitussive activity. These pharmacological activities can be proved by classic tests using the instant compounds on mammals such as the rat and the guinea-pig.

The compounds according to the present invention can be administered to mammals, such as the rat and guinea-pig, that present cardiac arrhythmia pictures, bronchospasm as to histamine or as a tussive agent, either rectally or orally or even parenterally, that is, by administering the particular compound according to the present invention to the host mammal rectally, orally or intravenously or intraperitoneally, in the form of suspensions or aqueous solutions in conventional manner.

The dosage of the instant compounds applicable for each such utility purpose or method of use generally ranges from 0.1 to 50 mg/kg per day, i.e. between about 0.1 and 50 mg per kg body weight of the host mammal per day, preferably between 0.5 and 30 mg/kg/day and in particular between 1 and 15 mg/kg per day. More particularly, such dosage preferably ranges from 2.5 to 50, and especially 2.5 to 30, mg/kg/day.

The antiarrhythmic action of the instant compounds has been measured, for example, by the test of arrhythmia for strophanthin K in the guinea-pig according to Sekiya and Vaughan Williams (Br. J. Pharmacol. 38, 749; 1963) and by the test of arrhythmia due to calcium chloride in the rat according to Grimaldi et al. (J. Pharm. Pharmacol. 33, 194; 1981); the calcium antagonist activity of the instant compounds has been demonstrated on the guinea-pig ventricle by the technique according to Mantelli et al. (Arch. Int. Pharmacodyn. Ther. 254, 99; 1981); the local anaesthetic activity of such compounds has been demonstrated in the rat by the technique according to Bianchi (Br.J. Pharmacol. Chemother. 11, 104; 1956); the antihistamitic activity of such compounds has been demonstrated in the guinea pig in form of an antagonist to the histamine aerosol (0.2% solution atomized under 0.2 atm.), that is, as demonstrated by the increase of the latency between the appearance of the typical bronchospastic response in animals which had received the compound under test and the controls; and the antitussive activity of such compounds has been evaluated as an antagonism of the cough induced in the cavity by inhalation of acrolein vapors (Silvestrini and Pozzetti, Arch. Int. Pharmacodyn. Ther. 129, 249; 1960); all such tests demonstrating significant effectiveness of the instant compounds for each corresponding utility purpose or method of use.

According to the described tests, the instant compounds have all shown the above mentioned pharmacological characteristics after oral or parenteral administration, that is, intraperitoneal or intravenous administration, which was observed after 15 minutes from the oral or parenteral administration.

According to the test results, the compounds of the present invention have proved to be useful as antiarrhythmic and antitussive agents or medicines, and, to a lesser extent, as $H_1$ antihistamines. In addition, the pharmacological action of calcium antagonistic type present in the compounds according to the present invention indicates that at least some of them can be advantageously used in the treatment of myocardium ischemic pathology and in the treatment of arterial hypertension (Ellrodt, Circulation 62, 669; 1980).

For example, the following Table sets forth the results of a typical test regarding antitussive activity for the above ordinally set forth compounds 1, 17 to 23, 40, 53 and 57, in comparison to the known compounds DROPROZINE and MORCLOPHON, such test having been effected in vivo on a two month old guinea pig by administering 10 mg/kg, i.e. 10 mg of the particular compound per kg of body weight, per os (by mouth) an hour prior to acrolein aerosol exposure according to the procedure set forth in Silvestrini and Pozzatti, Arch. Int. Pharmacodyn. Ther., 1960, 129, 249, with the antitussive inhibition activity having the following percent range values: $+ =$ Inhib. 20–25%, $++ =$ Inhib. 25–30%, and $+++ =$ Inhib. above 30%.

TABLE

| Compound Tested | Antitussive Activity |
|---|---|
| 1 | ++ |
| 17 | ++ |
| 18 | +++ |
| 19 | +++ |
| 20 | +++ |
| 21 | +++ |
| 22 | +++ |
| 23 | ++ |
| 40 | ++ |
| 53 | ++ |
| 57 | ++ |
| Droprozine | ++ |
| Morclophon | + |

Thus, an Inhib. above 30% antitussive activity value was exhibited by:

(18)
N,N-dimethyl-N'[(benzofuran-2-yl)(p-chlorophenyl)methyl]ethylenediamine hydrochloride,

(19)
N,N-dimethly-N'[(benzofuran-2-yl)(p-chlorophenyl)methyl]propylenediamine hydrochloride,

(20)
N,N-dimethyl-N'[(benzofuran-2-yl)(phenyl)methyl]ethylene diamine hydrochloride,

(21)
N[(benzofuran-2-yl)(p-chlorophenyl)methyl]-2(diethylmethylammonium) ethylamine bromide, and

(22)
N[(5-bromobenzofuran-2-yl)(phenyl)methyl]-N',N'-diethylethylenediamine hydrochloride.

As to the remaining compounds, an Inhib. of 25–30% antitussive activity value was exhibited by:

(1)
N,N-diethyl-N'-[(benzofuran-2-yl)(p-chlorophenyl)methyl]ethylenediamine dihydrochloride,

(17)
N,N-diethyl-N'-[(benzofuran-2-yl)(phenyl)methyl]ethylenediamine hydrochloride,

(23)
N-[(benzofuran-2-yl)(p-tolyl)methyl]-N',N'-diethylethylenediamine hydrochloride,

(40)
N,N-dimethyl-N'-[(benzofuran-2-yl)(p-fluorophenyl)methyl]ethylenediamine hydrochloride,

(53)
N,N-dimethyl-N'-[(5-bromobenzofuran-2-yl)(phenyl)methyl]ethylenediamine dihydrochloride, and

(57)
N,N,N'-trimethyl-N'-[(benzofuran-2-yl)(p-chlorophenyl)methyl]ethylenediamine dihydrochloride hydrate.

Hence, as is clear from the above Table, the instant compounds, as the case may be, are as active as, or higher in activity than, DROPROZINE but are all higher in activity than MORCLOPHON, as regards antitussive activity, i.e. a type of muscle relaxant activity.

All of the instant compounds possess similar such activity as well as the other activities as hereinabove indicated.

Thus, the compounds according to the present invention may be preferably employed in a method of treating an arrhythmic, histaminic or tussive condition, which comprises administering to a mammal suffering from such a condition, e.g. orally or parenterally or rectally, a corresponding antiarrhythmic, antihistaminic or antitussive effective amount of a composition containing a compound according to the present invention in association with a pharmaceutical carrier or excipient.

The carrier or excipient may be any conventional pharmaceutical carrier or excipient, e.g. water, starch or the like, and the compositions thereof with the compounds of the present invention may be prepared in conventional manner for oral, parenteral or rectal administration as the case may be.

More specifically, the compounds according to the present invention may be employed in a method of treating an arrhythmic, e.g. local anaesthetic treatable arrhythmic, or calcium antagonist treatable arrhythmic or cardiac muscle spasm treatable arrhythmic, condition; or of treating a histaminic, e.g. blockable $H_1$ histaminic, or bronchiospasm treatable histaminic, condition; or of treating a tussive, e.g. muscle spasm, or bronchiospasm, or coughing, condition; as the case may be, which comprises administering to a mammal suffering from such a condition, orally or parenterally or rectally, e.g. orally, intraperitoneally or intravenously, a correspondingly antiarrhythmic, e.g. local anaesthetic antiarrhythmic, or calcium antagonist antiarrhythmic, or cardiac muscle relaxant antiarrhythmic, effective amount; or a corresponding antihistaminic, e.g. blocking $H_1$ antihistaminic, or bronchiospasm antihistaminic, effective amount; or a corresponding antitussive, e.g. muscle relaxant, or bronchiospasm relaxant, or cough relaxant, effective amount; of a composition containing a compound according to the present invention as pharmaceutically active ingredient in association with a pharmaceutical carrier or excipient, as aforesaid.

In particular, the instant compounds may be employed in a method of treating a tussive or coughing condition, which comprises administering to a host mammal suffering from or prone to such a condition a muscle relaxant, or bronchiospasm relaxant, or cough relaxant, or antitussive, amount of a composition containing a compound according to the present invention as pharmaceutically active ingredient in association with a pharmaceutical carrier or excipient, as aforesaid.

Of course, the instant compounds may be used in the form of their corresponding pharmaceutically acceptable salts as well as in their free form.

It will be appreciated that in the above general formulas, as the case may be, $R_1$ and $R_2$ each individually may be hydrogen; a halogen atom such as Cl, Br, F and I; an alkyl group such as a lower alkyl group and especially an alkyl group having from 1 to 4 carbon atoms; an arylalkyl or aralkyl group such as a phenylalkyl, naphthylalkyl and the like group, especially a phenyl- and naphthyl-lower alkyl group, particularly a phenyl- and naphthyl-alkyl group having from 1 to 4 carbon atoms in the alkyl radical, more particularly a phenyl lower alkyl group, and most particularly a phenylalkyl group having 1 to 4 carbon atoms in the alkyl radical; an aryl group such as a phenyl, naphthyl and the like group, and particularly a phenyl group; hydroxyl; an alkoxy group such as a lower alkoxy group and especially an alkoxy group having from 1 to 4 carbon atoms; $NH_2$; an NH-alkyl group such as an NH-lower alkyl group and especially an NH-alkyl group having from 1 to 4 carbon atoms; an $N(alkyl)_2$ group such as an $N(lower\ alkyl)_2$ group and especially an $N(alkyl)_2$ group having from 1 to 4 carbon atoms in each alkyl radical, in all cases with the two corresponding alkyl radicals being the same or different; an NH(CO-alkyl) group such as an NH(CO-lower alkyl) group and especially an NH(CO-alkyl) group having from 1 to 4 carbon atoms in the alkyl radical; an NH (CO-aryl) group such as an NH(CO-phenyl), NH(CO-naphthyl) and the like group, and especially an NH (CO-phenyl) group; and $NO_2$; and when $R_1$ and $R_2$ are taken together they form a ring of 5 to 8 carbon atoms, e.g. fused to the benzofuranyl radical, and especially the group —CH=CH—CH=CH—; $R_1$ and $R_2$ each individually preferably being H; a halogen group; an alkoxy group; and when taken together preferably forming a ring of 5 to 8 carbon atoms; all as defined above;

$R_3$ may be hydrogen; an alkyl group having from 1 to 4 carbon atoms; and an aryl group as defined above and especially a phenyl group; $R_3$ preferably being hydrogen and an alkyl group having from 1 to 4 carbon atoms;

$R_4$ may be hydrogen; an alkyl group as defined above; an aryl group as defined above and especially a phenyl group; and an arylalkyl or aralkyl group as defined above, more particularly a phenyl lower alkyl group and most particularly a phenyl alkyl group having from 1 to 4 carbon atoms in the alkyl radical; $R_4$ preferably being hydrogen; an alkyl group; and an arylalkyl or aralkyl group; all as defined above;

$R_5$ may be hydroxyl; an alkoxy group as defined above; an OCO-alkyl group such as an OCO-lower alkyl group and especially and OCO-alkyl group having from 1 to 4 carbon atoms in the alkyl radical; an OCO-aryl group such as an OCO-phenyl, OCO-naphthyl and the like group, and especially an OCO-phenyl group; an OCO—NH-alkyl group such as an OCO—NH-lower alkyl group and especially an OCO—NH-alkyl group having 1 to 4 carbon atoms in the alkyl radical; an OCO—NH-aryl group such as an OCO—NH-phenyl, OCO—NH-naphthyl and the like group, and especially an OCO—NH-phenyl group; the group —$NR_7(CH_2)_nN(R_8)(R_9)$; the group —$N(R_8)(R_9)$; and the group $O(CH_2)_nN(R_8)(R_9)$; wherein n is a number between 1 and 4, i.e. from 1 to 4; $R_7$ may be hydrogen and an alkyl group having from 1 to 4 carbon atoms; and $R_8$ and $R_9$ each individually may be hydrogen; an alkyl group as defined above; an aryl group as defined above and especially a phenyl group; an alkoyl or alkanoyl group such as a lower alkanoyl group and especially an alkanoyl group having from 1 to 4 carbon atoms in the alkyl radical attached to the CO radical of the alkanoyl group; and an arylalkoyl or aralkanoyl group such as a phenylalkanoyl, naphthylalkanoyl and the like group, especially a phenyl- and naphthyl-lower alkanoyl group, particularly a phenyl- and naphthyl-alkanoyl group having from 1 to 4 carbon atoms in the alkyl radical attached between the phenyl or naphthyl radical and the CO radical of the aralkanoyl group, more particularly a phenyl lower alkanoyl group, and most particularly a phenylalkanoyl group having from 1 to 4 carbon atoms in the alkyl radical attached between the phenyl radical and the CO radical of the phenylalkanoyl group; an aroyl group such as a benzoyl, naphthoyl and the like group, and especially a benzoyl group; and when $R_8$ and $R_9$ are taken together they form a heterocyclic ring, which may optionally contain one or more supplementary or additional hetero atoms such as nitrogen, oxygen and the like, such as a piperidyl, morpholino, piperazino and the like heterocyclic ring, and which may optionally be substituted with one or more substituents such as an alkyl group as defined above; a hydroxyalkyl group such as a hydroxy lower alkyl group and especially a hydroxy alkyl group having 1 to 4 carbon atoms; an aryl group as defined above and especially a phenyl group; and a heterocyclic ring group as defined above such as a pyridyl group; especially with such a substituent being attached to an optionally present supplementary or additional hetero atom contained in the heterocyclic ring such as a nitrogen atom; $R_5$ preferably being hydroxyl; an OCO-NH-alkyl group; the group —$NR_7(CH_2)_nN(R_8)(R_9)$; and the group —$N(R_8)(R_9)$; all as defined above; and more preferably as to the groups —$NR_7(CH_2)_nN(R_8)(R_9)$ and —$N(R_8)(R_9)$ wherein $R_8$ and $R_9$ each individually may be hydrogen and an alkyl group as defined above; and wherein when $R_8$ and $R_9$ are taken together they form a heterocyclic ring as defined above; and $R_6$ may be hydrogen, a halogen atom as defined above; an alkyl group as defined above; an arylalkyl or aralkyl group as defined above, especially a phenyl alkyl group, more particularly a phenyl lower alkyl group and most particularly a phenyl alkyl group having from 1 to 4 carbon atoms in the alkyl radical; an aryl group as defined above and especially a phenyl group; hydroxyl; an alkoxy group as defined above; $NH_2$; an NH-alkyl group as defined above; an N(alkyl)$_2$ group as defined above; an NH(CO-alkyl) group as defined above; an NH(CO-aryl) group as defined above and especially an NH(CO-phenyl) group; and $NO_2$; $R_6$ preferably being hydrogen; a halogen atom; an alkyl group; an aryl group and especially a phenyl group; an alkoxy group; and $NO_2$; all as defined above.

More particularly, in this regard, as to the compounds of general formula II, these contemplate ketones in which preferably $R_1$ and $R_2$ each individually may be hydrogen and an alkoxy group; and when $R_1$ and $R_2$ are taken together they form a ring containing 5 to 8 carbon atoms; all as defined above;

$R_3$ is hydrogen; and $R_6$ may be hydrogen; a halogen atom; an aryl group and especially a phenyl group; an alkoxy group; and $NO_2$; all as defined above.

Correspondingly, as to the compounds of general formula I, these contemplate alcohols, carbamates and bases such as open or non-cyclic amine bases and cyclic amine bases or N-containing heterocyclic ring amine bases, i.e. both acyclic and cyclic amine bases, in which, as the case may be, preferably $R_1$ and $R_2$ each individually may be hydrogen; a halogen atom; and an alkoxy group and where $R_1$ and $R_2$ are taken together they may form a ring containing 5 to 8 carbon atoms; all as defined above;

$R_3$ may be hydrogen and an alkyl group as defined above;

$R_4$ may be hydrogen; an alkyl group; and an arylalkyl or aralkyl group, especially a phenyl lower alkyl group and particularly a phenylalkyl group having from 1 to 4 carbon atoms in the alkyl radical; all as defined above;

$R_5$ is hydroxyl in the case of alcohols;

$R_5$ is an OCO—NH-alkyl group as defined above, such as an N-alkylcarbamoyloxy group, especially an N-lower alkylcarbamoyloxy group, and more particularly an N-alkylcarbamoyloxy group having from 1 to 4 carbon atoms in the alkyl radical attached to the nitrogen atom, in the case of carbamates;

$R_5$ may be the group —$NR_7(CH_2)_nN(R_8)(R_9)$ and the group —$N(R_8)(R_9)$; wherein n and $R_7$ are as defined above; and $R_8$ and $R_9$ each individually may be hydrogen and an alkyl group as defined above; and wherein when $R_8$ and $R_9$ are taken together they form a heterocyclic ring as defined above, in the case of the bases; and $R_6$ may be hydrogen; a halogen atom; an alkyl group; an aryl group and especially a phenyl group; and $NO_2$; all as defined above.

More especially as to the alcohols according to general formula I, these contemplate compounds in which preferably $R_1$ and $R_2$ each individually may be hydrogen; a halogen atom; and an alkoxy group; and where $R_1$ and $R_2$ are taken together they may form a ring containing 5 to 8 carbon atoms; all as defined above;

$R_3$ may be hydrogen and an alkyl group as defined above;

$R_4$ may be hydrogen; an alkyl group; and an arylakyl or aralkyl group, especially a phenyl lower alkyl group and particularly a phenylalkyl group having from 1 to 4 carbon atoms in the alkyl radical; all as defined above;

$R_5$ is hydroxyl; and $R_6$ may be hydrogen; a halogen atom; an alkyl group; an aryl group and especially a phenyl group; and $NO_2$; all as defined above.

More especially as to the carbamates according to general formula I, these contemplate compounds in which preferably $R_1$, $R_2$, $R_3$ and $R_4$ are all hydrogen;

$R_5$ is an OCO—NH-alkyl group as defined above, such as an N-alkyl-carbamoyloxy group, especially an N-lower alkylcarbamoyloxy group, and more particularly an N-alkylcarbamoyloxy group having from 1 to 4 carbon atoms in the alkyl radical attached to the nitrogen atom; and

R$_6$ is a halogen atom as defined above.

More especially as to the open or non-cyclic or acyclic amine bases according to general formula I, these contemplate compounds in which preferably R$_1$ and R$_2$ each individually may be hydrogen and a halogen atom as defined above;

R$_3$ and R$_4$ are both hydrogen;

R$_5$ may be the group —NR$_7$(CH$_2$)$_n$N(R$_8$)(R$_9$) and the group —N(R$_8$)(R$_9$); wherein n and R$_7$ are as defined above; and R$_8$ and R$_9$ each individually may be hydrogen and an alkyl group as defined above; and R$_6$ may be hydrogen; a halogen atom; and an alkyl group; as defined above; and as to the cyclic amine bases or N-containing heterocyclic ring amine bases according to general formula I, these contemplate compounds in which preferably R$_1$, R$_2$, R$_3$ and R$_4$ are all hydrogen;

R$_5$ may be the group —NR$_7$(CH$_2$)$_n$N(R$_8$)(R$_9$) and the group —N(R$_8$)(R$_9$); wherein n and R$_7$ are as defined above; and R$_8$ and R$_9$ are taken together to form a heterocyclic ring as defined above; and R$_6$ may be hydrogen; a halogen atom; and an alkyl group; as defined above.

As to the open or non-cyclic or acyclic amine bases according to general formula I wherein R$_5$ is the group —NR$_7$(CH$_2$)$_n$N(R$_8$)(R$_9$), more preferably R$_1$ and R$_2$ each individually may be hydrogen and a halogen atom as defined above;

R$_3$ and R$_4$ are both hydrogen;

n and R$_7$ are as defined above; and R$_8$ and R$_9$ each individually may be hydrogen and an alkyl group as defined above; and R$_6$ may be hydrogen; a halogen atom; and an alkyl group; as defined above.

As to the open or non-cyclic or acyclic amine bases according to general formula I wherein R$_5$ is the group —N(R$_8$)(R$_9$), more preferably;

R$_1$, R$_2$, R$_3$ and R$_4$ are all hydrogen;

R$_8$ and R$_9$ each indivudally may be hydrogen and an alkyl group as defined above; and R$_6$ is a halogen atom.

As to the cyclic amine bases or N-containing heterocyclic ring amine bases according to general formula I wherein R$_5$ is the group —NR$_7$(CH$_2$)$_n$N(R$_8$)(R$_9$), more preferably R$_1$, R$_2$, R$_3$ and R$_4$ are all hydrogen;

n and R$_7$ are as defined above; and R$_8$ and R$_9$ are taken together to form a heterocyclic ring as defined above; and R$_6$ *is a halogen atom.*

As to the cyclic amine bases or N-containing heterocyclic ring amine bases according to general formula I wherein R$_5$ is the group —N(R$_8$)(R$_9$), more preferably R$_1$, R$_2$, R$_3$ and R$_4$ are all hydrogen;

R$_8$ and R$_9$ are taken together to form a heterocyclic ring as defined above; and R$_6$ may be hydrogen; a halogen atom; and an alkyl group; as defined above. More particularly as to the open or non-cyclic or acyclic amine bases, where R$_5$ is the group —NR$_7$(CH$_2$)$_n$N(R$_8$)(R$_9$), it may be preferably monoalkylamino (mono to tetramethylene) amino, dialkylamino (mono to tetra methylene) amino, monoalkylamino (mono to tetra methylene) (alkyl) amino and dialkylamino (mono to tetramethylene) (alkyl) amino, i.e. N'-alkyl or N',N'-dialkyl-N,N'-(mono to tetramethylene) amino and N'-alkyl or N',N'-dialkyl-N,N'-(mono to tetramethylene)-N-alkylamino, wherein each alkyl group is as defined above.

Correspondingly as to the open or non-cyclic or acyclic amine bases where R$_5$ is the group —N(R$_8$)(R$_9$), it may be preferably amino, i.e. unsubstituted amino, and mono or dialkyl amino, and especially amino and monoalkylamino, wherein each alkyl group is as defined above.

More particularly as to the cyclic amine bases or N-containing heterocyclic ring amine bases where R$_5$ is the group —NR$_7$(CH$_2$)$_n$N(R$_8$)(R$_9$), it may be preferably morpholino (mono to tetra methylene) amino and morpholino (mono to tetra methylene)(alkyl) amino, e.g. N'-morpholino-N,N'-(mono to tetramethylene) amino and N'-morpholino-N,N'-(mono to tetramethylene)-N-alkylamino, and especially N'-morpholino-N-N'-(monto to tetramethylene) amino, wherein each alkyl group is as defined above.

Correspondingly, as to the cyclic amine bases or N-containing heterocyclic ring amine bases where R$_5$ is the group —N(R$_8$)(R$_9$), it may be preferably piperidyl, morpholino, alkyl-piperazino, hydroxy alkyl-piperazino, aryl-piperazino and especially phenyl-piperazino, and pyridyl-piperazino, e.g. N-piperidyl, N-morpholino, N'-alkyl-N-piperizino, N'-hydroxyalkyl-N-piperazino, N'-aryl-N-piperazino and especially N'-phenyl-N-piperazino, and N'-(C-pyridyl)-N-piperazino, wherein each alkyl and aryl moiety is as defined above.

We claim:

1. A compound selected from the group consisting of compounds having the formula

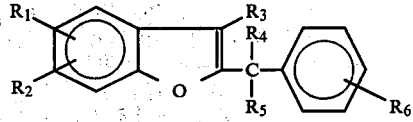

and pharmaceutically acceptable salts thereof, in which:

R$_1$ and R$_2$ are selected from the group consisting of a hydrogen atom, a halogen atom, an alkyl group containing 1 to 4 carbon atoms, a phenyl lower alkyl group, a naphthyl lower alkyl group, a phenyl group, a naphthyl group, a hydroxyl group, a lower alkoxy group, an NH$_2$ group, an NH-lower alkyl group, an N(lower alkyl)$_2$ group, an NH(CO-lower alkyl) group, an NH(CO-phenyl) group, an NH(CO-naphthyl) group, and an NO$_2$ group, and a ring of 5–8 carbon atoms including both R$_1$ and R$_2$;

R$_3$ is selected from the group consisting of a hydrogen atom, an alkyl group containing 1 to 4 carbon atoms, a phenyl group and a naphthyl group;

R$_4$ is selected from the group consisting of a hydrogen atom, a lower alkyl group, a phenyl group, a naphthyl group, a phenyl lower alkyl group and a naphthyl lower alkyl group;

R$_5$ is an

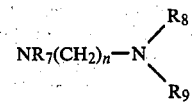

group in which n is an integer of from 1 to 4, R$_7$ is selected from the group consisting of a hydrogen atom and an alkyl group containing from 1 to 4 carbon atoms, and $R_8$ and $R_9$ are selected from the group consisting of a hydrogen atom, a lower alkyl group, a phenyl group, a naphthyl group, a lower alkanoyl group, a phenyl lower alkanoyl group, a naphthyl lower alkanoyl group, a benzoyl group and a naphthoyl group; and $R_6$ is selected from the group consisting of a hydrogen atom, a halogen atom, a lower alkyl group, a phenyl lower alkyl group, a naphthyl lower alkyl group, a phenyl group, a naphthyl group, a hydroxyl group, a lower alkoxy group, an $NH_2$ group, an NH-lower alkyl group, an N(lower alkyl)$_2$ group, an NHCO-lower alkyl group, an NHCO-phenyl group, and NHCO-naphthyl group and an $NO_2$ group.

2. A compound according to claim 1, wherein $R_1$ and $R_2$ are each selected from the group consisting of hydrogen, halogen and lower alkoxy, and when $R_1$ and $R_2$ are taken together they form a ring of 5–8 carbon atoms, $R_3$ is selected from the group consisting of hydrogen and alkyl containing 1 to 4 carbon atoms, $R_4$ is selected from the group consisting of hydrogen, lower alkyl, phenyl lower alkyl, and naphthyl lower alkyl, $R_8$ and $R_9$ are each selected from the group consisting of hydrogen and lower alkyl, and $R_6$ is selected from the group consisting of hydrogen, halogen, lower alkyl, phenyl, naphthyl, lower alkoxy and $NO_2$.

3. A compound according to claim 1, wherein $R_1$ and $R_2$ are the same.

4. A compound according to claim 1, wherein $R_1$ and $R_2$ are different.

5. A compound according to claim 1, wherein $R_8$ and $R_9$ are the same.

6. A compound according to claim 1, wherein $R_8$ and $R_9$ are different.

7. A compound according to claim 1, which contain one or more asymmetric carbon atoms, in optically active form.

8. A compound according to claim 1, selected from the group consisting of

N,N-diethyl-N'-[(benzofuran-2-yl)(p-chlorophenyl) methyl]ethylenediamine and pharmaceutically acceptable salts thereof, N,N-diethyl-N'-[(benzofuran-2-yl)(phenyl) methyl]ethylenediamine and pharmaceutically acceptable salts thereof, N,N-dimethyl-N'-[(benzofuran-2-yl)(p-chlorophenyl)methyl]ethylenediamine and pharmaceutically acceptable salts thereof, N,N-dimethyl-N'-[(benzofuran-2-yl)(p-chlorophenyl) methyl]propylene-diamine and pharmaceutically acceptable salts thereof, N,N-dimethyl-N'[(benzofuran-2-yl)(phenyl) methyl]ethylenediamine and pharmaceutically acceptable salts thereof, N-[(benzofuran-2-yl)(p-chlorophenyl)methyl)]2-(diethylmethylammonium)ethylamine bromide and other pharmaceutically acceptable salts thereof, N-[(5-bromo-benzofuran-2-yl)(phenyl)methyl]-N',N'-diethylethylenediamine and pharmaceutically acceptable salts thereof, N-[(benzofuran-2-yl)(p-tolyl)methyl]-N',N'-diethylenediamine and pharmaceutically acceptable salts thereof, N,N-dimethyl-N'-[(benzofuran-2-yl)(p-fluorophenyl) methyl]ethylenediamine and pharmaceutically acceptable salts thereof, N,N-dimethyl-N'-[(5-bromobenzofuran-2-yl) (phenyl) methyl]ethylenediamine and pharmaceutically acceptable salts thereof, and N,N,N'-trimethyl-N'-[(benzofuran-2-yl) (p-chlorophenyl)methyl]ethylenediamine and pharmaceutically acceptable salts thereof.

9. A compound according to claim 1, wherein $R_1$ and $R_2$ are each selected from the group consisting of hydrogen and halogen, $R_3$ and $R_4$ are both hydrogen, $R_8$ and $R_9$ are selected from the group consisting of hydrogen and lower alkyl, and $R_6$ is selected from the group consisting of hydrogen, halogen and lower alkyl.

10. A compound according to claim 1, wherein the compound is N,N-diethyl-N'-[(benzofuran-2-yl)(p-chlorophenyl) methyl]ethylenediamine dihydrochloride.

11. A pharmaceutical composition comprising an anti-arrhythmic, or anti-histaminic, or anti-tussive, amount of at least one compound as claimed in claim 1 as active ingredient, in association with a member selected from the group consisting of carriers and excipients.

12. A composition according to claim 11, in suitable form for administration by a method selected from the group consisting of oral, parenteral and rectal administration.

13. A composition according to claim 12, in the form of a unit dose.

14. A composition according to claim 11, in the form of a unit dose.

15. A method of treating an arrhythmic, histaminic or tussive condition, which comprises administering to a mammal suffering from such a condition a correspondingly effective amount of a composition according to claim 11.

16. A method of treating a tussive condition, which comprises administering to a mammal suffering from such a condition a muscle relaxant effective amount of a composition according to claim 11.

* * * * *